(12) United States Patent
Boguszewski et al.

(10) Patent No.: US 6,490,909 B1
(45) Date of Patent: Dec. 10, 2002

(54) METHOD AND APPARATUS FOR CALCULATING CARBON CONTENT OF FLY ASH

(75) Inventors: Stanley Boguszewski, Russell, MA (US); Joseph W. Quinn, Bloomfield, CT (US)

(73) Assignee: ABB Automation Inc., Wickliffe, OH (US)

( * ) Notice: Subject to any disclaimer, the term of this patent is extended or adjusted under 35 U.S.C. 154(b) by 284 days.

(21) Appl. No.: 09/659,979

(22) Filed: Sep. 12, 2000

(51) Int. Cl.⁷ .............................................. G01N 22/00
(52) U.S. Cl. ..................................................... 73/23.33
(58) Field of Search ............................. 73/23.31, 23.33, 73/28.01; 364/497; 324/633, 636, 637; 250/338.5, 339.05, 339.06, 343

(56) References Cited

U.S. PATENT DOCUMENTS 5,177,444 A * 1/1993 Cutmore ..................... 324/637
5,369,369 A * 11/1994 Cutmore ..................... 324/637
5,729,470 A * 3/1998 Baier ........................ 364/497

* cited by examiner

Primary Examiner—Robert Raevis
(74) Attorney, Agent, or Firm—Michael M. Rickin, Esq.

(57) ABSTRACT

A method and apparatus for calculating the volume fraction of carbon in the fly ash using a carbon in fly ash sensor that has a resonant cavity. The method first determines the volume fraction of ash in the fly ash. The method then determines the real and imaginary components of the dielectric constant of a mixture of pure carbon and pure fly ash, and the transmission factor of a signal from the oscillator in the sensor transmitted through the cavity due to absorption by material in the cavity. The method then determines the volume fraction of carbon in the fly ash by using the volume fraction of ash, the real and imaginary components of the pure mixture dielectric constant, the absorption transmission factor and the length of the cavity, the speed of light and the frequency of the oscillator.

6 Claims, 5 Drawing Sheets

METHOD AND APPARATUS FOR CALCULATING CARBON CONTENT OF FLY ASH

FIELD OF THE INVENTION

This invention relates to sensors that measure the Carbon content of the fly ash produced by the combustion process in a pulverized coal-fired steam generator and more particularly to the calculation of the carbon content sensed by such a sensor.

DESCRIPTION OF THE PRIOR ART

Fly ash results from the incomplete combustion of pulverized coal in a pulverized coal-fired steam generator. The fly ash is the combination of inert and inorganic residue resulting from the incomplete combustion of the pulverized coal. The pulverized coal contains varying amounts of carbon or coke particles. In general, the inorganic ash particles consist primarily of silicates, oxides and sulfates, together with small quantities of phosphates and other trace compounds.

The presence of unburned Carbon in boiler fly ash has important economic and environmental consequences to the operator of a coal-fired boiler installation. Its presence is a measure of inefficient fuel utilization which means that more fuel must be burned in order to obtain a given output and which in turn directly increases the cost of electrical power generation. Furthermore, inefficient fuel utilization by virtue of requiring more fuel to be burned in order to produce a given output increases the presence of $NO_x$ emissions which is the basis for environmental concerns. Thus, knowledge of the Carbon content of boiler fly ash is an important element in establishing a low $NO_x$ boiler emission strategy.

In addition, low Carbon fly ash can be a potential source of income to the operator of a pulverized coal-fired boiler in that fly ash can be employed as a building material if the Carbon content in the fly ash is sufficiently low. Fly ash with a high Carbon content is unsuitable as a building material and normally requires the use of expensive waste disposal methods.

One system for continuous in-situ measurement of Carbon in fly ash is described in U.S. Pat. No. 5,729,470 ("the '470 Patent") which is assigned to the same assignee as the present invention. The system described in the '470 Patent includes a resonant cavity for measuring in-situ and in real time the Carbon content of the fly ash.

Referring now to FIG. 1 (which is FIG. 5 of the '470 Patent), there is shown the resonant cavity 300 in the system of the '470 Patent. Also shown in FIG. 1, are intelligence 100, transmitting section 200 and receiving section 400 of the system of the '470 Patent. As is shown in FIG. 2 herein (which is FIG. 3 of the '470 Patent), intelligence 100 includes a CPU 112.

Returning once again to FIG. 1, the transmitting section 200 includes a pressure boundary 202, an oscillator 204, a signal coupler 208, a reference detector 210, a signal isolator 214 and a waveguide 216.

The transmitting section 200 further includes a first air purge 218 and a second air purge 220.

The cavity section 300 is comprised of a first concave spherical mirror 302, a second concave spherical mirror 304, a common optical axis 306, a plurality of alignment screws 308, an inspection volume 300', a first annular ring 302' and a second annular ring 304'. As is shown in FIG. 3 (which is FIG. 6 of the '470 Patent) the first and second concave spherical mirrors 302, 304 each contain a pattern of circular holes that are drilled therethrough that consist of a central hole 310, so located as to be on the optical axis 306, which is common both to the first concave spherical mirror 302 and the second concave spherical mirror 304 and an array of planetary holes 312 symmetrically located about the central hole 310.

As is shown in FIG. 4 (which is FIG. 7 of the '470 Patent) the first and second concave spherical mirrors 302, 304 have attached to their nonreflecting sides three screws 308 symmetrically located about the center of the mirrors 302, 304 for the purpose of aligning said mirrors 302, 304 along the common optical axis 306. Two of three alignment screws 308 for each of mirrors 302, 304 are turned by an associated stepper motor (not shown in FIG. 1).

The receiving section 400 includes a pressure boundary 402, a waveguide 404 and a signal detector 408. The receiving section 400 further includes a first air purge 412 and a second air purge 414.

The oscillator 204 receives as input the electrical drive signal 104 originating from the intelligence section 100. The oscillator 204 typically may take the form of a free running biased tuned microwave oscillator, the nature of the construction and the mode of operation of which is known and understood by those skilled in the art. As a consequence of the input received thereby, the oscillator 204 generates as output a constant amplitude, sinusoidal signal 206 of electromagnetic radiation which repeatedly sweeps through a certain frequency span, $\Delta f$.

The oscillator output signal 206 is supplied in known fashion to the signal coupler 208. Again in known fashion, a small fraction 206' of the oscillator output signal 206 is diverted by the signal coupler 208 to the reference detector 210, to be described hereinafter, and the remainder 206" of the oscillator output signal 206 is supplied to the waveguide 216 via the signal isolator 214. Typically the signal isolator 214 may take the form of a waveguide section filled with a ferrite material so aligned that in combination with the magnetic field of a permanent magnet, electromagnetic radiation can propagate in one direction only. The purpose of the signal isolator 214 is to prevent signal return from the cavity section 300. Since reflected energy is sharply attenuated by the signal isolator 214 it helps ensure the frequency and amplitude stability of the oscillator 204.

The detector 210 is designed to receive as input the signal 206' which is delivered from the signal coupler 208 in the form of electromagnetic radiation and whose power is a small fraction of the oscillator signal 206 power. The reference detector 210 typically may take the form of a full wave rectifier which may or may not be followed by a peak detector. The reference detector 210 is operative upon the input signal 206' in a known manner in order to thereby generate as output a reference signal 212 in the nature of a DC voltage proportional to the power of the input signal 206' that is supplied to the reference detector 210.

The signal 206" in the form of electromagnetic radiation is supplied as an input to the waveguide 216 which, in accordance with the best mode embodiment of the invention, is rigidly fixed to the non-reflecting side of the first concave spherical mirror 302 so as to be aligned along the common optical axis 306. The waveguide 216 in turn is designed so as to be operative to deliver the signal 206" to the cavity section 300 via the central hole 310 which is illustrated in FIG. 3. The waveguide 216, in accordance with the best mode embodiment of the invention, is preferably equipped with a first air purge 218. The air purge 218 is designed to be operative so as to direct an external source of pressurized air 218' into and along the waveguide 216 through to the cavity section 300 via the central hole 310 depicted in FIG. 3. Such purging activity helps prevent fouling of the mirror 302 and the waveguide 216 which might otherwise occur due to fly ash buildup.

The transmitting section 200 includes a pressure boundary 202. The pressure boundary 202 may or may not enclose the oscillator 204, the signal coupler 208, the reference detector 210 and the signal isolator 214. The pressure boundary 202 coupled with the first spherical mirror 302 and an annular ring 302' concentric with the mirror 302 is intended to define a volume 202' which undergoes purging similar to that which has been described above. Such purging directs an external source of pressurized air 220' into the aforesaid volume 202' through to the cavity section 300 via the annular ring 302' and the planetary holes 312 shown in FIG. 3. The purging activity helps prevent fouling of the mirror 302 which might otherwise occur due to fly ash buildup.

The cavity section 300 includes the first concave spherical mirror 302 and the second concave spherical mirror 304, each aligned along the common optical axis 306 and so oriented that their reflective sides face one another. For purposes of the description thereof the cavity section 300 further is considered to encompass the approximately cylindrical inspection volume 300' subtended by the concave spherical mirrors 302, 304, as the latter are separated by a fixed distance, L, along the common optical axis 306, and an imaginary boundary not shown in FIG. 1 but shown in FIG. 9 of the '470 Patent delimited by the beam spot size, w(z). It is through and across this inspection volume 300' that the flue gas stream 28 is made to flow, carrying with it boiler fly ash.

As described hereinabove, the sinusoidal signal 206" of electromagnetic radiation is supplied to the cavity section 300 from the transmitting section 200 via the waveguide 216. The signal 206" enters the inspection volume 300' from the center hole 310 depicted in FIG. 3. The signal 206" propagates through the inspection volume 300' to the second concave spherical mirror 304 and is reflected back to the first concave spherical mirror 302 to be reflected once again back to the second concave spherical mirror 304. To this end the signal 206" is reflected back and forth between the two spherical mirrors 302, 304 numerous times. The resulting steady state signal 206" is captured by the second concave spherical mirror 304 at the center hole 310 shown in FIG. 3. The signal 206" is then delivered by way of the waveguide 404 to the signal detector 408. The waveguide 404, in accordance with the best mode embodiment of the invention, preferably is rigidly fixed to the non-reflecting side of the second concave spherical mirror 304 so as to be aligned along the common optical axis 306.

The signal detector 408 receives as input, from the cavity section 300, the signal 206" that is in the form of electromagnetic radiation. Typically the signal detector 408 may take the form of a full wave rectifier which may or may not be followed by a peak detector. The signal detector 408 is operative upon the input signal 206" in known fashion to provide as an output therefrom, a cavity signal 410 which is in the nature of a DC voltage that is proportional to the power of the input signal 206" to the signal detector 408. The cavity signal 410 then functions as one input to the intelligence section 100.

It is further seen from reference to FIG. 1 that the receiving section 400 includes a pressure boundary 402. The pressure boundary 402 may or may not enclose the signal detector 408. The pressure boundary 402 coupled with the second concave spherical mirror 304 and an annular ring 304', concentric with the second concave spherical mirror 304, define a volume 402' which, preferably in accordance with the best mode embodiment of the invention, undergoes purging from an external source of pressurized air 414' similar to that which has been described hereinabove, with respect to the transmitting section 200. Furthermore, the waveguide 404 that directs the captured signal 206" to the signal detector 408 also, preferably in accordance with the best mode embodiment of the invention, undergoes a purging process from an external source of pressurized air 412' similar to that which has been described hereinabove, with respect to the transmitting section 200. Such purging helps prevent fouling of the mirror 304 and waveguide 404 as a result of fly ash buildup, which might otherwise occur.

The component elements of the resonant cavity are affixed to the rear gas pass of the pulverized coal-fired steam generator by rigidly fixing the pressure boundaries 202, 402 by any type of conventional means suitable for use for such purpose, to the opposing walls of the rear gas pass at nearly the same elevation. The first and second concave spherical mirrors 302, 304 of the cavity section 300 are in turn mounted to the pressure boundaries 202, 402 via the alignment screws 308 so as to be capable of mutual alignment along the common optical axis 306 by way of the alignment screws 308. It should be noted that the first and second concave spherical mirrors 302, 304 are not affixed directly to the walls of the rear gas pass.

As the transmitted signal 206" is swept through its frequency span, Δf, and reflected back and forth between the mirrors 302, 304, one or more cavity resonances may be excited. The resonances are typified by repetitive, sharp peaks in the power of the transmitted signal 206" detected at the receiver 408. A resonance profile representative of resonant cavities is shown in FIG. 5 (which is FIG. 8 of the '470 Patent). Such a data profile is presented to the central processing unit 112, via the data signal(s) 110. As is described in the '470 Patent, the purpose of CPU 112 is to process the signals 110 to thereby characterize any resonances excited within cavity 300.

The '470 Patent describes the use of a calibration curve so that the carbon loading can be obtained from the peak amplitude A of the signal received at receiver 408. The curve is generated by comparing known samples to peak amplitude and since the curve is nonlinear it has proven difficult to generate accurately in practice. Further the system of the '470 Patent uses free spectral range to measure ash loading which is not easy to obtain from a microwave system. The method of the present invention solves overcomes these problems.

SUMMARY OF THE INVENTION

The present invention is a method for determining the volume fraction of carbon of fly ash using a sensor that has a resonant cavity that is excited by an oscillator. The method has the steps of:

a) calculating the volume fraction of ash Vfash in the fly ash; and b) calculating the volume fraction of carbon in fly ash from:

$$Vfcarbon = \frac{-b \pm \sqrt{b^2 - 4(ac)}}{2(a)^2}$$

where $$a = \left( \frac{-2\pi Lf(Vfash)\varepsilon'' carbon}{C(\ln(Ta))} \right)^2$$

$$b = Vfash(\varepsilon' ash - \varepsilon' carbon)$$

$$c = (-Vfash(\varepsilon' ash) - 1')$$

and L is the length of the resonant cavity, C is the speed of light in meters per second and f is the frequency of the oscillator.

The present invention is also an apparatus for determining the volume fraction of carbon of fly ash using a sensor that has a resonant cavity that is excited by an oscillator. The apparatus has:

a) a digital processor; and
b) a routine executed by the digital processor for:
(i) calculating the volume fraction of ash Vfash in the fly ash; and
(ii) calculating the volume fraction of carbon in fly ash from:

c)

$$Vfcarbon = \frac{-b \pm \sqrt{b^2 - 4(ac)}}{2(a)^2}$$

where $$a = \left( \frac{-2\pi Lf(Vfash)\varepsilon'' carbon}{C(\ln(Ta))} \right)^2$$

$$b = Vfash(\epsilon' ash - \epsilon'' carbon)$$

$$c = (-Vfash(\epsilon' ash) - 1')$$

and L is the length of the resonant cavity, C is the speed of light in meters per second and f is the frequency of the oscillator.

DESCRIPTION OF THE PREFERRED EMBODIMENT(S)

Figure 6:
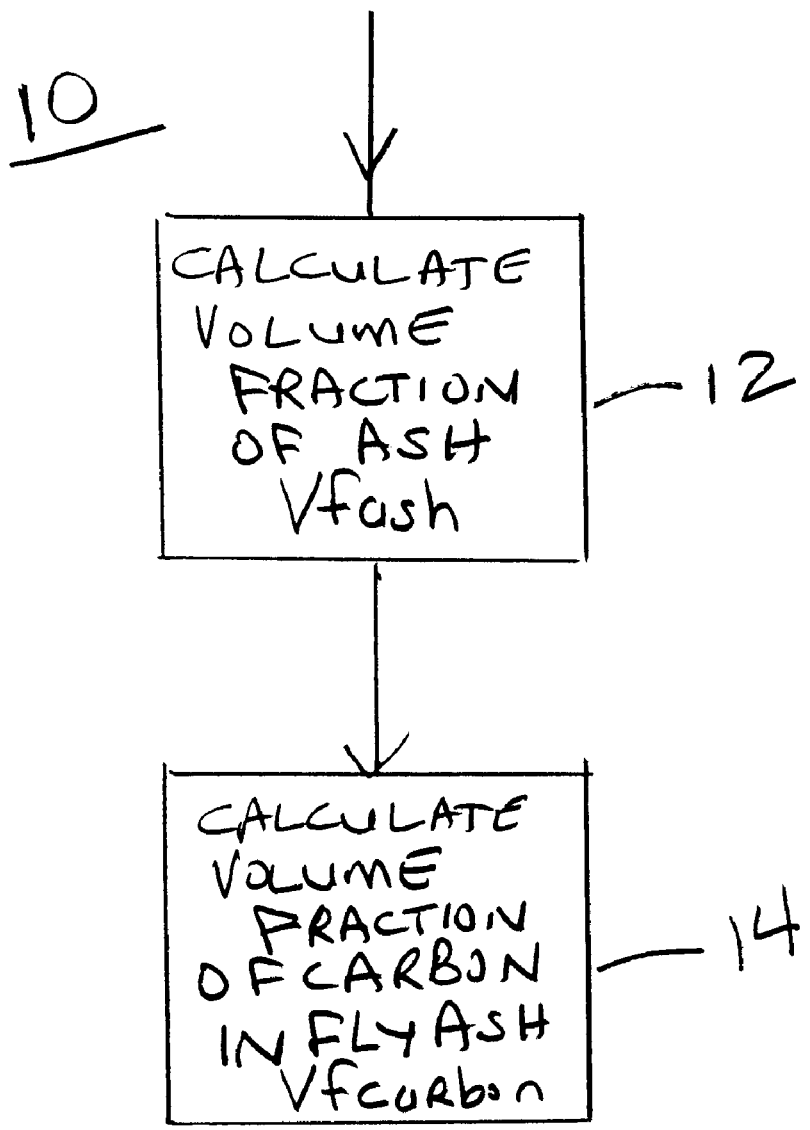
FIG. 6 shows a flowchart for the Carbon in ash calculation method of the present invention.

Referring now to FIG. 6 there is shown a flowchart for the method 10 of the present invention that calculates the amount of Carbon in the fly ash. The method is executed in CPU 112.

The first step 12 in the method is the calculation of the volume fraction of ash, Vfash, using the formula:

$$Vfash = \frac{ash\_loading}{density\_of\_ash}$$

where ash_loading is the amount of ash in the flue gas in grams per cubic meter (gm/m3) as measured by a commercially available instrument known as a dust probe which can be purchased from the assignee of the present invention, and the density_of_ash is 2.931e6 gm/m3.

Figure 1:
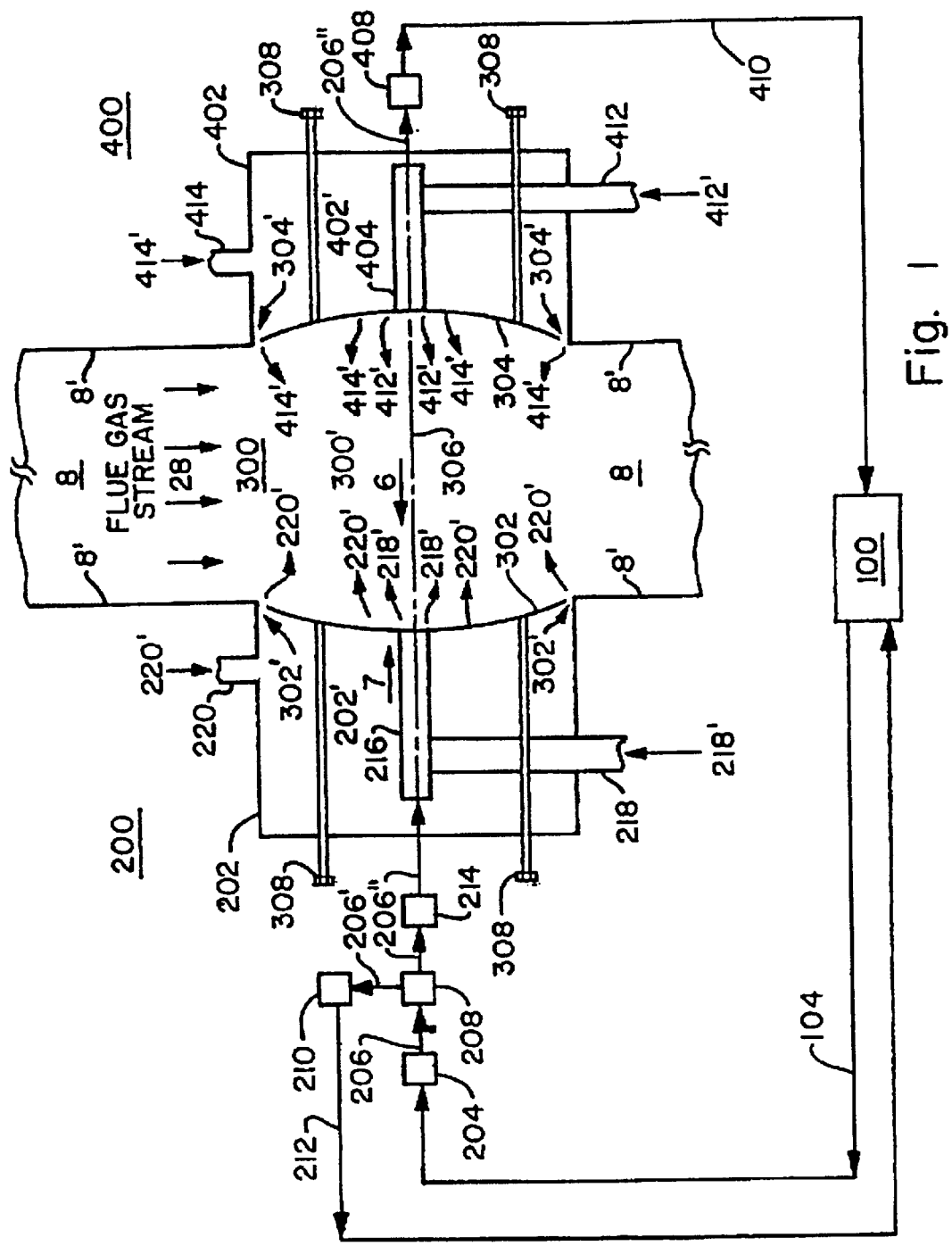
FIG. 1 shows the resonant cavity, and the intelligence, transmitting and receiving sections of the prior art Carbon in ash sensor.
Figure 2:
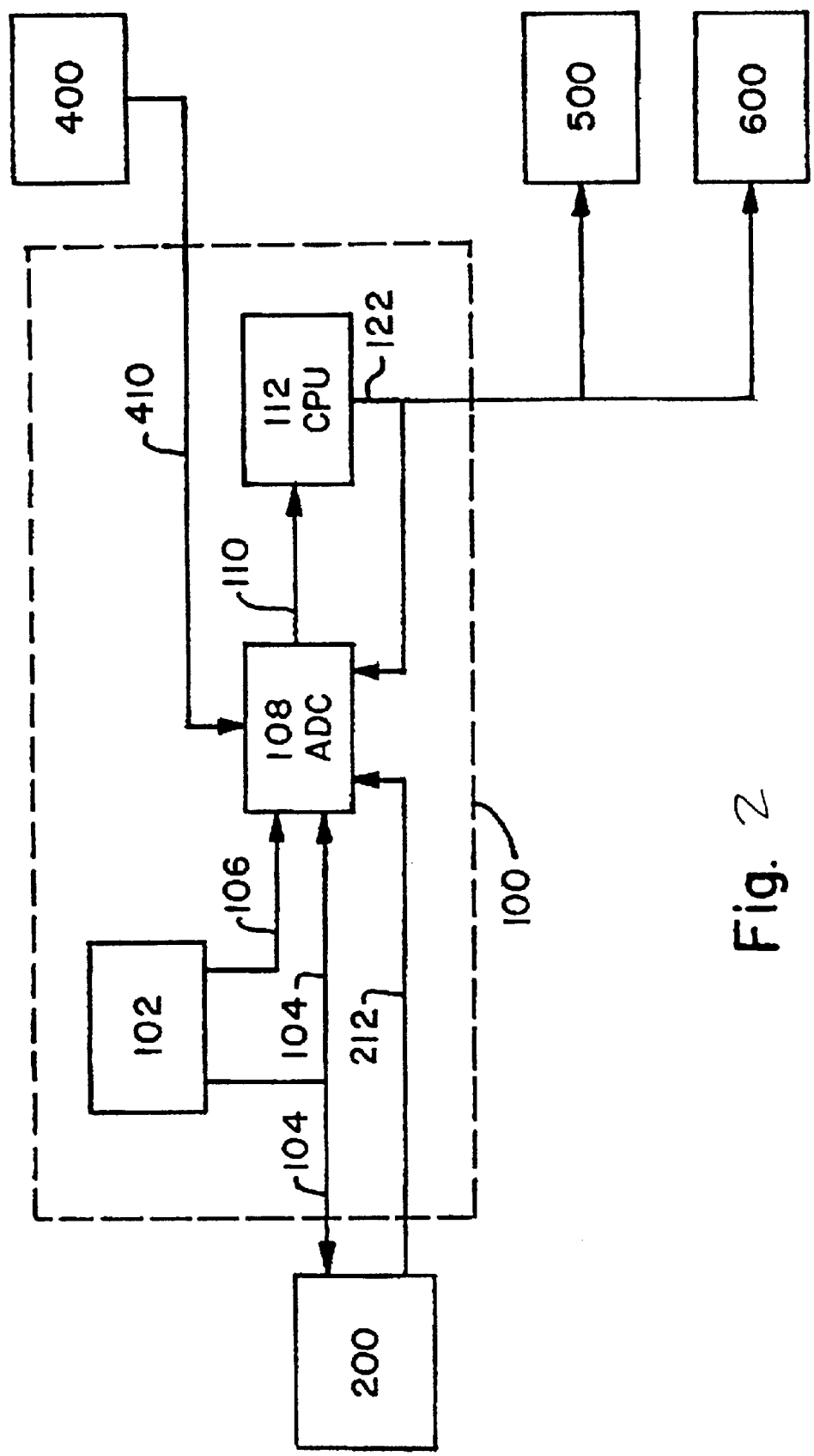
FIG. 2 shows a block diagram of the intelligence section of FIG. 1.
Figure 3:
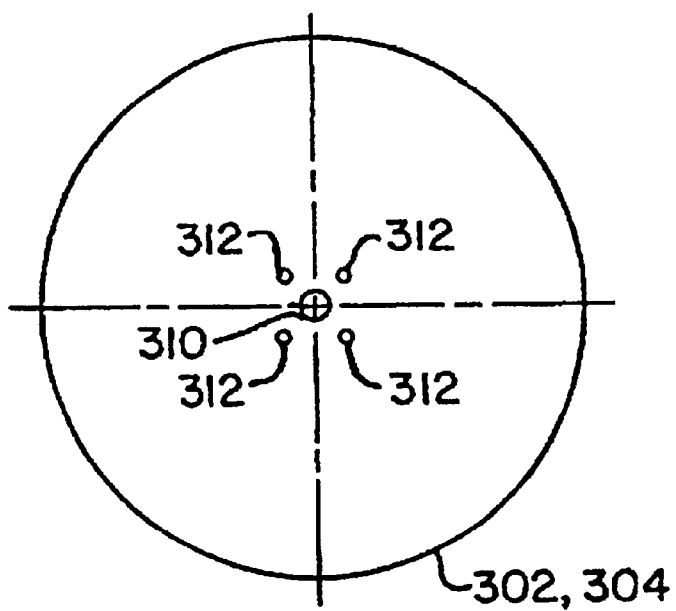
FIG. 3 shows a vertical sectional view of the reflecting surface of the mirrors shown in FIG. 1.
Figure 4:
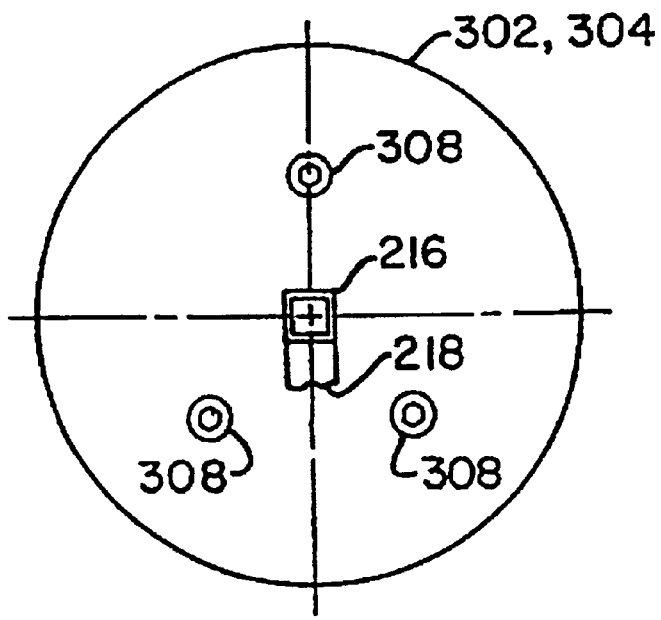
FIG. 4 shows a vertical sectional view of the nonreflecting surface of the mirrors shown in FIG. 1.
Figure 5:
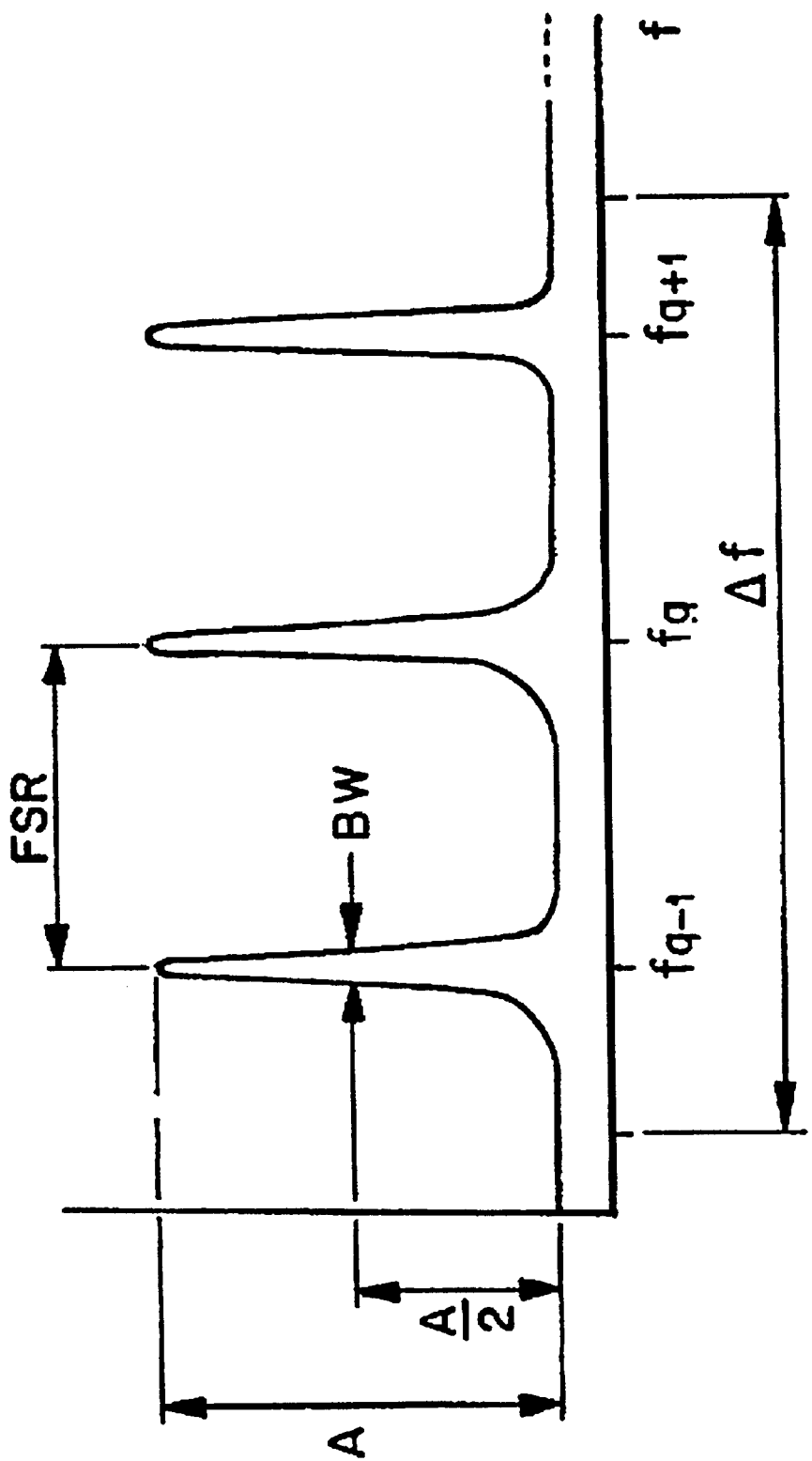
FIG. 5 is a graphical representation of resonance profiles typical of resonant cavities.

The method then proceeds to step 14 where it calculates, as is described in more detail below, the volume fraction of Carbon in the fly ash, vfcarbon, using among other parameters the transmission factor, Ta, of the signal 206" of electromagnetic radiation through resonant cavity 300 due to absorption by material in the cavity. Ta is obtained by using the peak amplitude A (see FIG. 5) of the signal detected at receiver 408 from the equation:

$$Ta = m(A) + b$$

where m and b are set during calibration of the Carbon in ash sensor.

As those of ordinary skill in the art can appreciate, the relationship of transmission factor Ta to the peak amplitude A of the detected signal is a linear relationship. This linear relationship allows a calibration curve that relates Ta to A to be easily generated using only a few test points. In contrast thereto, the calibration curve described in the '470 Patent that relates the peak amplitude to the volume of Carbon in the fly ash is nonlinear and has proven in practice to be difficult to generate accurately. Thus the method of the present invention in using Ta in the calculation of the volume fraction of Carbon in the fly ash provides a more accurate measure of that volume than the technique described in the '470 Patent.

The transmission factor Ta can also be expressed as a function of the length L of the resonant cavity 300, the speed of light C in meters per second, the frequency f of the oscillator 204, and the real and imaginary components of the dielectric constant of a mixture of pure carbon and pure ash, $\epsilon'$ mix and $\epsilon''$ mix respectively, as follows:

$$Ta = e^{-2L\left(\frac{\pi f \epsilon'' mix}{C\sqrt{\epsilon' mix}}\right)}$$

As is well known to those in the art, $\epsilon'$ mix and $\epsilon''$ mix are determined from:

$$\epsilon' mix = 1 + Vfash((1 - fcarbon)\epsilon' ash + fcarbon(\epsilon' carbon))$$

$$\epsilon'' mix = Vfash(fcarbon)\epsilon'' carbon$$

where $\epsilon'$ ash and $\epsilon'$ carbon are the real components of the dielectric constants of pure ash and pure carbon which have the values of 2.0 and 20.0, respectively; $\epsilon''$ carbon is the imaginary component of the dielectric constant of pure carbon, sometimes referred to as the absorption factor, which has the value of 1.45; and fash+fcarbon=1.

Substituting the equations shown above for $\epsilon'$ mix and $\epsilon''$ mix in the equation shown above for Ta and using mathematical manipulation techniques well known to those of ordinary skill in the art gives rise to the following equation for calculating volume fraction of Carbon in the fly ash Vfcarbon:

$$Vfcarbon = \frac{-b \pm \sqrt{b^2 - 4(ac)}}{2(a)^2}$$

where $$a = \left(\frac{-2\pi Lf(Vfash)\varepsilon'' carbon}{C(\ln(Ta))}\right)^2$$

$b=Vf\text{ash}(\epsilon'\text{ ash}-\epsilon'\text{ carbon})$ $c=(-Vf\text{ash}(\epsilon'\text{ ash})-1')$ In step 14 the method of the present invention uses the above equation to calculate the volume fraction of Carbon in the fly ash vfcarbon.

After the volume fraction of Carbon in the fly ash vfcarbon is calculated, the Carbon in the fly ash as a percent weight CIA can be calculated as follows:

$$CIA = \left(\frac{Vfcarbon \times pcarbon}{pash + (Vfcarbon(pcarbon - pash))}\right) \times 100$$

where pash is the density of ash and pcarbon is the density of Carbon.

Further the carbon loading Carbon_Loading can be calculated as follows:

Carbon_Loading=Vfcarbon×pcarbon

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A method for determining the volume fraction of carbon of fly ash using a sensor that has a resonant cavity that is excited by an oscillator comprising the steps of:
   d) calculating the volume fraction of ash Vfash in said fly ash; and
   e) calculating said volume fraction of carbon in fly ash from:

$$Vfcarbon = \frac{-b \pm \sqrt{b^2 - 4(ac)}}{2(a)^2}$$

where $$a = \left(\frac{-2\pi Lf(Vfash)\varepsilon'' carbon}{C(\ln(Ta))}\right)^2$$

$b=Vf\text{ash}(\epsilon'\text{ ash}-\epsilon'\text{ carbon})$ $c=(-Vf\text{ash}(\epsilon'\text{ ash})-1')$ and L is the length of said resonant cavity, C is the speed of light in meters per second and f is the frequency of said oscillator.

2. The method of claim 1 further comprising the step of calculating the Carbon in the fly ash as a percent weight from:

$$CIA = \left(\frac{Vfcarbon \times pcarbon}{pash + (Vfcarbon(pcarbon - pash))}\right) \times 100.$$

3. The method of claim 1 further comprising the step of calculating the carbon loading from:

Carbon_Loading=Vfcarbon×pcarbon.

4. Apparatus for determining the volume fraction of carbon of fly ash using a sensor that has a resonant cavity that is excited by an oscillator, said apparatus comprising:
   c) a digital processor; and
   d) a routine executed by said digital processor for:
      (iii) calculating the volume fraction of ash Vfash in said fly ash; and
      (iv) calculating said volume fraction of carbon in fly ash from:
   f)

$$Vfcarbon = \frac{-b \pm \sqrt{b^2 - 4(ac)}}{2(a)^2}$$

where $$a = \left(\frac{-2\pi Lf(Vfash)\varepsilon'' carbon}{C(\ln(Ta))}\right)^2$$

$b=Vf\text{ash}(\epsilon'\text{ ash}-\epsilon'\text{ carbon})$ $c=(-Vf\text{ash}(\epsilon'\text{ ash})-1')$ and L is the length of said resonant cavity, C is the speed of light in meters per second and f is the frequency of said oscillator.

5. The apparatus of claim 4 wherein said routine executed by said digital processor is also for calculating the Carbon in the fly ash as a percent weight from:

$$CIA = \left(\frac{Vfcarbon \times pcarbon}{pash + (Vfcarbon(pcarbon - pash))}\right) \times 100.$$

6. The apparatus of claim 4 wherein said routine executed by said digital processor is also for calculating the carbon loading from:

Carbon_Loading=Vfcarbon×pcarbon.

* * * * *